United States Patent [19]
Chou et al.

[11] Patent Number: 5,834,225
[45] Date of Patent: Nov. 10, 1998

[54] METHOD, DEVICE AND TEST KIT FOR CAPACITATION OF SPERM

[75] Inventors: Kuo-Chuan Karen Chou, Okemos, Mich.; Chai Ching Shirley Lin, Ilan, Taiwan

[73] Assignee: Board of Trustees operating Michigan State University, East Lansing, Mich.

[21] Appl. No.: 784,090

[22] Filed: Jan. 15, 1997

[51] Int. Cl.⁶ .............................. C12Q 1/54; C12Q 1/00; C12Q 1/32; C12Q 1/30

[52] U.S. Cl. .................... 435/14; 435/4; 435/2; 435/26; 435/27; 435/29; 435/283.1; 422/50; 422/68.1

[58] Field of Search ............................ 435/14, 4, 2, 26, 435/27, 29, 283.1; 422/50, 68.1

[56] References Cited

U.S. PATENT DOCUMENTS

| | | | |
|---|---|---|---|
| Re. 34,326 | 7/1993 | van Blerkom | 435/14 |
| 4,683,213 | 7/1987 | Ax et al. | 435/14 |
| 4,747,703 | 5/1988 | Ax et al. | 435/14 |
| 5,028,526 | 7/1991 | Deutsch | 435/14 |
| 5,185,246 | 2/1993 | Deutsch | 435/14 |
| 5,219,729 | 6/1993 | Hodgen | 435/14 |
| 5,250,417 | 10/1993 | Feuchter et al. | 435/14 |
| 5,389,519 | 2/1995 | Bronson | 435/14 |
| 5,474,890 | 12/1995 | Di Virgilio et al. | 435/14 |
| 5,554,604 | 9/1996 | Bonfils et al. | 435/14 |

OTHER PUBLICATIONS

Hoppe, P.C., Biol. Reprod. 15:39–45 (1976).
Fraser, L. R., et al., J. Reprod. Fertil. 61:25–35 (1981).
Sakkas, D., et al., Biol. Reprod. 49:1288–1292 (1993).
Whittingham, D.G., Nature 220:592–593 (1968).
Whittingham, D.G., J. Reprod. Fertil. Suppl. 14:7–21 (1971).
Fraser, L.R., J. Reprod. Fertil. 69:539–553 (1983).
Oehninger, S., et al., J. Assisted Reprod. Genetics, 12(1):41–47 (1995).
Badway, J.A., et al., Ann Rev. Biochem. 49:695–726 (1980).
Smith, R.M., et al., Blood 77:673–686 (1991).
Ward, C.R., et al., Dev. Biol. 104:287–296 (1984).
Chou, K., and R.M. Cook, Bull Environ. Contam. Toxicol. 54:251–257 (1995).

*Primary Examiner*—Louis N. Leary
*Attorney, Agent, or Firm*—Ian C. McLeod

[57] ABSTRACT

A method, medical device (10) and test kit for capacitation of sperm for fertilizing eggs in vitro or in vivo, is described. The sperm is particularly from lower mammals, such as domestic animals and wild animals to be bred in captivity. The capacitated sperm is also useful in research relating to the nature of capacitation of sperm following modification of the head of the sperm upon capacitation.

23 Claims, 7 Drawing Sheets

METHOD, DEVICE AND TEST KIT FOR CAPACITATION OF SPERM

BACKGROUND OF THE INVENTION

(1) Summary of the Invention

The present invention relates to a method, device and test kit for on demand capacitation of sperm of a lower mammal which is capacitated in vivo by glucose. The invention uses glucose substitutes which are unable to capacitate the sperm, but which acts as a carbohydrate energy source. Hydrogen peroxide or other reactive oxygen sources are then used to capacitate the sperm using a reactive oxygen species from the oxygen source. The capacitated sperm can then be used for research, fertilization of an egg in vitro or artificial insemination.

(2) Description of Related Art

Glucose has been shown to be essential for capacitation and fertilization of mouse gametes (Hoppe, P. C., Biol. Reprod. 15:39–45 (1976); Fraser, L. R., et al., J. Reprod. Fertil; 61:25–35 (1981); and Sakkas, D., et al., Biol. Reprod. 49:1288–1292 (1993)). No other carbohydrate tested, including fructose, lactate, and pyruvate, could substitute for glucose in supporting fertilization. Glucose has been implicated in the initiation of the acrosome reaction and the whiplash motility of spermatozoa associated with fertilizing ability (Fraser, L. R., et al., J. Reprod. Fertil. 61:25–35 (1981)). Culture media that are frequently used to support maximum in vitro fertilization, such as modified Krebs-Ringer bicarbonate solution (Whittingham, D. G., Nature 220:592–593 (1968)), M-16 medium (Whittingham, D. G., J. Reprod. Fertil. Suppl 14:7–21 (1971)) and modified Tyrode's medium (Fraser, L. R., J. Reprod. Fertil. 69:539–553 (1983)), contain three carbohydrates: pyruvate, lactate and glucose. Glucose alone is known to support maximum capacitation and fertilization (Hoppe, P. C., Biol. Reprod. 15:39–45 (1976)), while pyruvate or lactate alone does not. Furthermore, despite the ability of mouse spermatozoa to metabolize fructose, little fertilizing ability was supported by fructose alone (Hoppe, P. C., Biol. Reprod. 15:39–45 (1976); Fraser, L. R., et al., J. Reprod. Fertil. 61:25–35 (1981)).

Recently, other researchers have studied the role of reactive oxygen species in sperm fertilizing ability. Superoxide anion, generated by exogenous xanthine and xanthine oxidase, has been demonstrated to trigger human sperm hyperactivation and capacitation (Oehninger, S., et al., J. Assisted Reprod. Genetics, 12(1):41–47 (1995); Badway, J. A., et al., Ann Rev. Biochem. 49:695–726 (1980); Smith, R. M., et al., Blood 77:673–686 (1991); and Ward, C. R., et al., Dev. Biol. 104:287–296 (1984)). Hydrogen peroxide has also been shown to promote human (00075; 00086) and hamster sperm capacitation (C0023) in vitro. Glucose is believed to have a role in supporting sperm fertilizing ability as a substrate for NADPH production in the pentose phosphate pathway. NADPH oxidase is responsible for the production of superoxide anion ($O_2^{-}$), which is then converted to $H_2O_2$ (Badway, J. A., and M. L. Karnovsky, Ann Rev. Biochem. 49:695–726 (1980); Smith, R. M., and J. T. Curnutte, Blood 77:673–686 (1991); 00084).

The capacitation of human sperm is believed to be capacitated in a different manner than in lower mammals. Glucose is not considered to be essential and may even be detrimental. Human sperm an be capacitated by a reactive oxygen species.

Of general interest in the prior art are U.S. Pat. Nos. 4,683,213 and 4,747,703 to Ax et al; 5,028,526 and 5,185,246 to Deutsch et al and 5,474,890 to DiVirgilio et al. These patents relate to capacitation of sperm. U.S. Pat. No. RE 34,326 to van Blerkom describes encapsulated sperm which can be mixed with the reagents of the present invention for use in vitro or for insemination.

There is a need for a reliable method for on demand capacitation of sperm of lower mammals for fertilization of eggs on demand which does not rely upon glucose in a capacitation media, since glucose alone acts to capacitate the sperm.

OBJECTS

It is therefore an object of the present invention to provide a method, a device and test kit for capacitation of sperm on demand. It is further an object of the present invention to provide a method which is economical and highly reliable. These and other objects will become increasingly apparent by reference to the following description and the drawings.

DESCRIPTION OF PREFERRED EMBODIMENTS

Figure 1A:
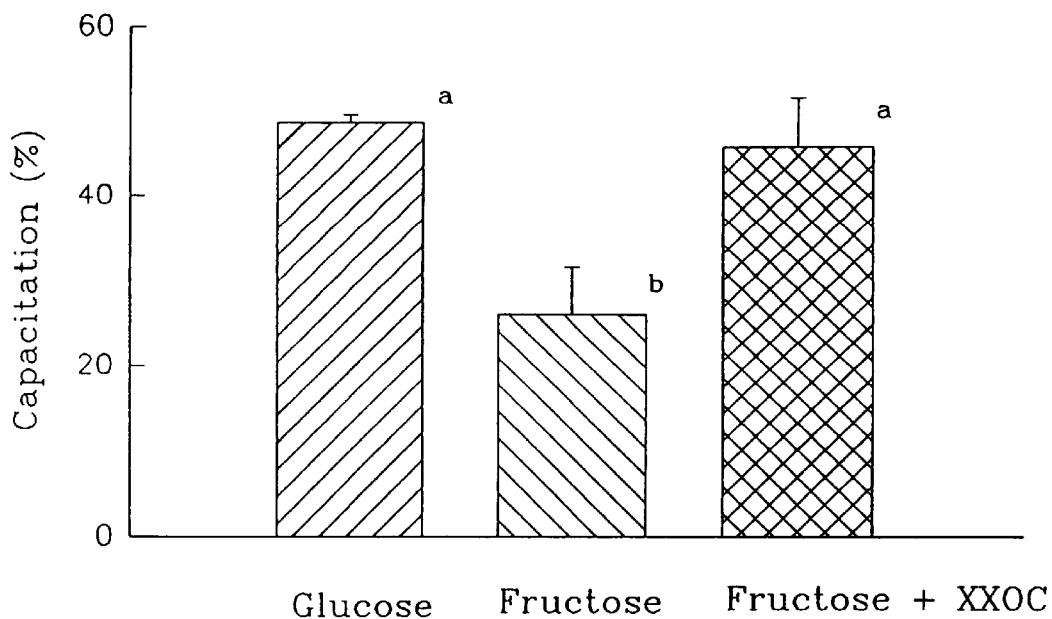
FIGS. 1A and 1B are graphs showing the percentage of capacitated (FIG. 1A) and acrosome reacted (FIG. 1B) spermatozoa in the media of glucose, fructose, or fructose with xanthine, xanthine oxidase and catalase (XXOC), using a chlortetracycline assay. Capacitated sperm displayed bright fluorescence over the anterior portion of the head and midpiece with a band which lacked fluorescence at the posterior portion of the head. At least 100 sperm per sample were examined at 45 min of sperm incubation. Acrosome reacted sperm displayed bright fluorescence on the midpiece and diminished fluorescence over the entire head. At least 100 sperm per sample were examined at 90 min of sperm incubation. (ab—Means with different superscripts differ ($p<0.05$).

The present invention relates to a method for capacitating sperm for fertilization of an egg which comprises:
  (a) providing a sperm sample which is substantially free of glucose, reactor oxygen species and preferably inhibitors of reactive oxygen species and containing an exogenous glucose substitute carbohydrate source which is unable to capacitate the sperm in the absence of reactive oxygen species; and
  (b) adding an exogenous capacitating agent which comprises the reactive oxygen species, preferably selected from the group consisting of sources of hydrogen peroxide and superoxide anion, to the sperm sample, whereby the sperm is capacitated for fertilization of the egg.

Further, the present invention relates to a method for fertilizing an egg with sperm which comprises:
  (a) providing a sperm sample which is substantially free of glucose and reactive oxygen species and containing an exogenous glucose substitute carbohydrate source which is unable to capacitate the sperm in absence of the reactive oxygen species;
  (b) adding exogenous capacitating agent which comprises the reactive oxygen species to the sperm sample whereby the sperm sample is capacitated for fertilization of the egg; and
  (c) fertilizing the egg with the capacitated sperm.

Further still, the present invention relates to an apparatus for capacitating sperm for fertilization which comprises providing in container (A) a sperm sample which is substantially free of glucose and reactive oxygen species and containing an exogenous glucose substitute carbohydrate source which is unable to capacitate the sperm in absence of the reactive oxygen species; and providing in a container (B) a capacitating agent which comprises the reactive oxygen species so that the sperm can be capacitated by mixing (A) and (B).

Finally, the present invention relates to a test kit for detecting an ability of sperm in a sample to be capacitated wherein the sperm is substantially free of glucose and reactive oxygen species which comprises:
  (a) a glucose substitute carbohydrate source which is unable to capacitate the sperm in absence of the reactive oxygen species;
  (b) a container (A) containing an exogenous capacitating agent which comprises a reactive oxygen species which can capacitate the sperm; and
  (c) a container (B) containing a fluorescent reagent which reacts with the sperm to produce a detectable indication of capacitation of the sperm and thus the ability to be capacitated.

Glucose has been considered to be essential for capacitation and fertilization of mouse gametes in vitro. Although glucose-6-phosphate (G-6-P) also supported maximum fertilization, no other simple carbohydrate tested, including fructose, fructose-6-phosphate (F-6-P), pyruvate and lactate, did so. However, in the presence of xanthine, xanthine oxidase, and catalase (XXOC) or $H_2O_2$, which produced a reactive oxygen species, fructose or F-6-P supported maximum fertilization.

Effects of XXOC, $H_2O_2$, and carbohydrates on sperm capacitation and the acrosome reaction were examined with the chlortetracycline (CTC) fluorescence assay. Glucose, but not fructose, supported the maximum rate of sperm capacitation and acrosome reaction. However, fructose in the presence of XXOC or $H_2O_2$ also supported maximum progress capacitation and acrosome reaction. Both insufficient and excessive amounts of $H_2O_2$ decreased sperm capacitation and acrosome reaction.

To examine the relationship between glucose and $H_2O_2$ production in sperm cells, 6-aminonicotinamide, a pentose phosphate pathway inhibitor, and apocynin, a NADPH oxidase inhibitor, were added to sperm suspension in glucose-containing medium. Sperm capacitation and the acrosome reaction were inhibited by either inhibitors. This supported the hypothesis that glucose, in addition to being an energy source, facilitates sperm capacitation and the acrosome reaction by generating $H_2O_2$ through the pentose phosphate pathway and the activity of NADPH oxidase.

The capacitating agent is hydrogen peroxide preferably in an amount between about 0.01 and 1 mM. An amount of 0.3 mM is most preferred. The combination of xanthine (X), xanthine oxidase (XO) and catalase (C) produces superoxide anion. The reactants are used in amounts which use up the xanthine. The xanthine is preferably used in an amount between about 0.05 mM and 0.250 mM, preferably about 0.125 mM. The incubations are for a time period between about 30 min and several hours, depending on the species.

Glucose forms glucose 6-phosphate which reacts with glucose-6-phosphate (G-6-P) dehydrogenase to generate NADPH, a substrate for NADP oxidase. These generate superoxide and then $H_2O_2$. Inhibitors can be used to interfere with this reaction and prevent the formation of reactive oxygen species which capacitate the sperm. The NADPH or the G-6-P dehydrogenase occurring in the sample can be inhibited. In this manner the capacitation of the sperm can be controlled until the sperm is to be used.

Exogenous glucose substitutes were used to provide energy without capacitating the sperm. Preferably these are fructose or fructose-6-phosphate, neither of which alone can capacitate the sperm in the absence of reactive oxygen species. Other carbon sources are pyruvate or lactate. These compounds are preferably used in an amount between about 0.1 and 100 mM. The carbon compounds can also enable the sperm to be preserved by freezing or maintaining a suitable temperature prior to use.

The sperm is isolated from lower mammals (non-human) where glucose is a precursor to capacitation, usually in the female reproductive tract, such as in mouse, rats, boar, cattle, equine, and wild mammals in captivity. The sperm of many domestic and wild mammals can be examined using the present invention to identify the rate of glucose and reactive oxygen species in modulating the progress of sperm capacitation, particularly those bred in captivity. The non-glucose capacitated sperm can be combined with the egg in vitro or in vivo by artificial insemination. The sperm can be used for research to show capacitation.

Figure 7:
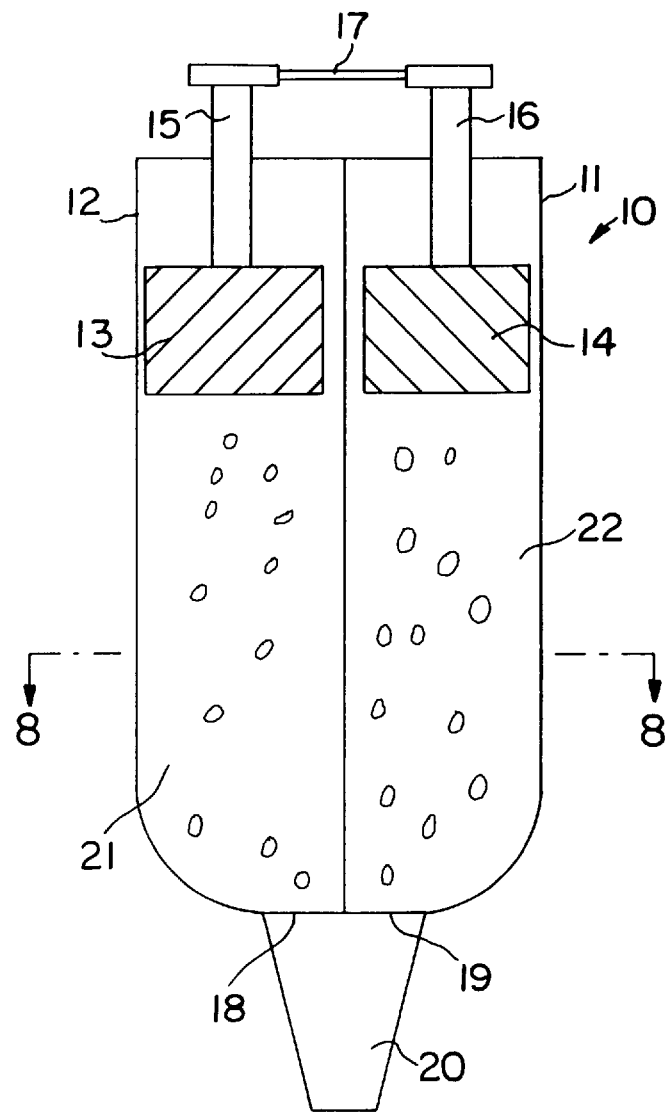
FIG. 7 is a front cross-sectional view of an apparatus for dispensing together a mixture of (1) the sperm and (2) a capacitating agent according to the present invention.
Figure 8:
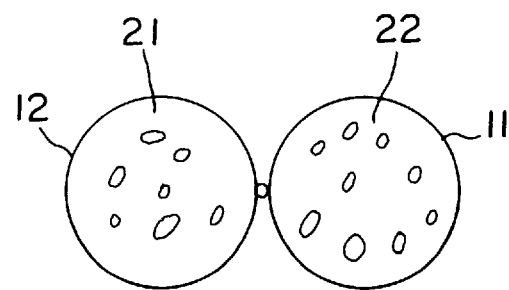
FIG. 8 is a cross-sectional view along line 8—8 of FIG. 7.

FIGS. 7 and 8 show a device 10 for capacitating the sperm. It incudes two (2) syringes with barrels 11 and 12 which are coupled together, each having plungers 13 and 14 moved by rods 15 and 16 joined together by connector 17. Membranes 18 and 19 are provided at the distal ends of the barrels 11 and 12 leading to a common chamber 20 so that the combined sperm 21 and capacitating agent 22 can be mixed for use in vivo or in vitro. The membranes 18 and 19 are ruptured during mixing.

The following are non-limiting examples of the present invention.

MATERIALS AND METHODS

Materials

The test media, containing different carbohydrates were modified based on M-16 medium (Whittingham, D. G., J. Reprod. Fertil.; Suppl 14:7–21 (1971)). Original M-16 contains 5.56 mM D-glucose, 22 mM Na-lactate, 0.33 mM Na-pyruvate, 40 mg/ml BSA, 94.66 mM NaCl, 1.19 mM $K_2HPO_4$, 4.78 mM KCl, 1.71 mM $CaCl_2.2\ H_2O$, 1.19 mM $MgSO_4\ .7\ H_2O$, 25 mM $NaHCO_3$, 100 IU/ml Penicillin G. (K salt), and 100 IU/ml Streptomycin sulphate. The media were adjusted to pH 7.4. All chemicals were purchased from Sigma (St. Louis, Mo.).

In vitro Fertilization

Epididymal spermatozoa were collected from mature $B_6D_2$-$F_1$ mice and incubated with test medium at 37° C., 5 $CO_2$ in air, and 100% humidity before being used for insemination.

Oocytes in cumulus mass were collected from superovulated $B_6D_2$-$F_1$ females 21–42 days of age. Superovulation was achieved by intraperitoneal injections of 10 IU pregnant mare serum gonadotropin (PMSG) followed 48–50 h later by 10 IU hCG. Oocytes in cumulus mass were collected into test media from ampulla 12 to 13 h after hCG injections. Spermatozoa, after 1.5 h preincubation in the test medium, were added to newly collected oocytes and incubated for 24 h before fertilization was examined. The final sperm concentration at insemination was $1–5 \times 10^6$ cells/ml.

To examine fertilization, eggs were stained with 37 $\mu$M bisBenzimide Hoechst No. 33258 (Sigma, St. Louis, Mo.) for 0.5 h before they were examined with a Nikon OPTIPHOT (Japan) microscope, equipped with a 100 W mercury bulb, 365/10 nm excitation filter, 400 nm dichroic mirror, and 400 nm barrier filter. Eggs containing 2-cells with a nucleus in each cell were recorded as fertilized. Eggs with one cell and two pronuclei were also recorded as fertilized. Eggs containing only one cell and one nucleus were considered non-fertilized. Fragmented and degenerated eggs were also considered non-fertilized.

Treatments

EXAMPLE 1

In the first of a series of experiments, M-16 medium was modified to contain only one of the carbohydrates at the indicated concentration: 5.56 mM glucose, 5.56 mM fructose, 5.56 mM fructose-6-phosphate (F-6-P), 5.56 mM glucose-6-phosphate (G-6-P), 5.56 mM Na-pyruvate, 22 mM Na-pyruvate, or 22 mM Na-lactate. When glucose, lactate, or pyruvate was eliminated from M-16 medium, additional NaCl was added to maintain osmolarity (Fraser, L. R., et al., J. Reprod. Fertil. 61:25–35 (1981)).

RESULTS

In M-16 medium, 83.9±6.4% of eggs were fertilized. In the presence of glucose or G-6-P alone, 88.6±7.6% and 77.9±5.5% of the eggs were fertilized, respectively (Table 1). The absence of pyruvate and lactate did not significantly change the percentage of fertilized eggs. As in previous studies (Hoppe, P. C. biol. Reprod. 15:39–45 (1976); Fraser, L. R., et al., J. Reprod. Fertil. 61:25–35 (1981); and Sakkas, D., et al., Biol. Reprod. 49:1288–1292 (1993)), when fructose, pyruvate, or lactase alone was present in the medium, no fertilization occurred (Table 1).

TABLE 1

Effect of individual carbohydrates on sperm fertilizing ability.

| Source of carbohydrates | No. of eggs observed | Eggs fertilized (%)[a] |
|---|---|---|
| Control[b] | 129 | 83.9 ± 6.4[c] |
| Glucose (5.56 mM) | 111 | 88.6 ± 7.6[c] |
| G-6-P (5.56 mM) | 74 | 77.9 ± 5.5[c] |
| Fructose (5.56 mM) | 110 | 1.6 ± 1.4[d] |
| F-6-P (5.56 mM) | 61 | 1.1 ± 2.1[d] |
| Pyruvate (5.56 mM) | 87 | 1.2 ± 2.1[d] |
| Pyruvate (22 mM) | 96 | 1.9 ± 1.7[d] |
| Lactate (22 mM) | 68 | 1.9 ± 3.2[d] |

[a]After 90 min of preincubation, spermatozoa were incubated with eggs for 2 hours. Eggs were then washed with fresh medium and incubated for another 22 hours before examination for fertilization. Values are means ± S.E.M. of 3 experiments.
[b]Control medium, M-16, contained 5.56 mM glucose, 0.33 mM pyruvate, and 22 mM lactate.
[c,d]Means with different superscripts differ ($p < 0.05$).

EXAMPLE 2

In the second series of experiments, 0.125 mM xanthine (X) and 0.0125 units/ml xanthine oxidase (XO) were added to the sperm suspension. After incubation for 15 min, 34 $\mu$g/ml catalase (C) was added to selectively remove $H_2O_2$ (Oehninger, S., et al., J. Assisted Reprod. Genetics 12(1) :41–47 (1995); Badway, J. A., et al., Ann. Rev. Biochem. 49:695–726 (1980); and Smith, R. M., et al., Blood 77:673–686 (1991)). Spermatozoa were then incubated for a total of 90 min before insemination. After 2 h, eggs were washed with fresh medium and incubated for another 22 h before examination for fertilization. At 45 min and 90 min of preincubation sperm capacitation and the acrosome reaction were examined with chlortetracycline (CC) fluorescence assay (Ward, Cr. R., and B. T. Story, Dev. Biol. 104:287–296 (1984); and Chou, K., and R. M. Cook, Bull Environ. Contam. Toxicol. 54:251–257 (1995)).

To test the hypothesis that glucose supports sperm fertilizing ability by generating reactive oxygen species, glucose in the medium was substituted with xanthine, xanthine oxidase, and catalase (XXOC). In the absence of carbohydrates, XXOC alone did not support fertilization (Table 2). When XXOC was combined with fructose, F-6-P, or glucose, maximum fertilization was obtained. The combination of XXOC with pyruvate or lactate supported fertilization up to 42.1±7.1% and 41.1±1.0%, respectively, which is about half of the fertilization supported by fructose with XXOC, F-6-P with XXOC, glucose with XXOC, G-6-P, or glucose alone.

TABLE 2

Fertilization of mouse gametes in the presence of xanthine oxidase system and carbohydrates.

| Treatment | No. of eggs observed | Eggs fertilized (%)[a] |
|---|---|---|
| Glucose (5.56 mM) | 87 | 88.5 ± 3.2[d] |
| Glucose (5.56 mM), XXOC[b] | 90 | 86.7 ± 2.5[d] |
| Fructose (5.56 mM), XXOC | 83 | 87.1 ± 4.0[d] |
| F-6-P (5.56 mM), XXOC | 33 | 79.1 ± 7.3[d] |
| Pyruvate (5.56 mM), XXOC | 74 | 37.0 ± 6.0[e] |
| Pyruvate (22 mM), XXOC | 51 | 42.1 ± 7.1[e] |
| Lactate (22 mM), XXOC | 83 | 41.1 ± 1.0[e] |
| XXOC only[c] | 91 | 0[f] |

[a]After 90 minutes of preincubation, spermatozoa were incubated with eggs for 2 hours. Eggs were then washed with fresh medium and incubated for another 22 hours before examination for fertilization. Values are means ± S.E.M. of 3 experiments.
[b]XXOC represents the xanthine oxidase system: xanthine (X), xanthine oxidase (XO), and catalase (C). Spermatozoa were incubated with X and XO for 15 minutes before addition of catalase. They were then incubated for 75 minutes before being used for fertilization.
[c]No carbohydrate was present in the medium.
[d,e,f]Means with different superscripts differ (p < 0.05).

EXAMPLE 3

In the third series of experiments, different concentrations of $H_2O_2$ from 0.025 mM to 5 mM were added with 5.56 mM fructose to the test media. The results were used to determine the optimal concentration of $H_2O_2$ in glucose free medium for fertilization. Sperm capacitation, the acrosome reaction as well as sperm motion parameters were examined at three selected $H_2O_2$ concentrations. For the sperm motion assay, a 20 μl aliquot of sperm suspension taken at 90 min of incubation was placed on a CEKKSIFT 20 μm chamber and analyzed with a CELLSOFT computer-assisted digital image analysis system (CRYO Resources Inc., New York, 1986). A minimum of 100 sperm cells were analyzed to obtain percent of motile spermatozoa and curvilinear velocity.

Figure 1B:
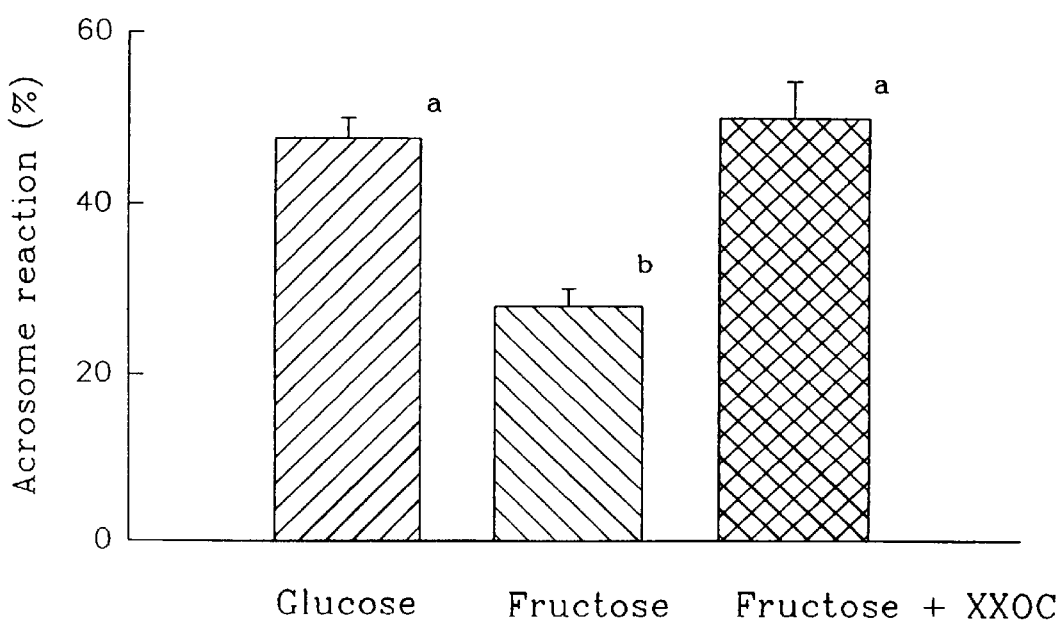

The percentages of capacitated and acrosome reacted spermatozoa in fructose alone were significantly lower (p<0.05) than those in either glucose or fructose with XXOC (FIG. 1).

When catalase was eliminated from the fructose and XXOC treatment, only 14.5±3.7% of the eggs were fertilized (Table 3). Fructose and catalase without XXO also did not support fertilization. Therefore, the combination of XXO with catalase, which converts $H_2O_2$ to $H_2O$, was necessary to achieve maximum fertilization, suggesting possible deleterious effects of excess $H_2O_2$ on spermatozoa. This observation, however, does not indicate if small amounts of $H_2O_2$, generated from XXOC, played a role in supporting sperm fertilizing ability in the absence of glucose.

TABLE 3

Effect of catalase in xanthine oxidase system on fertilization.

| Treatment | No. of eggs observed | Eggs fertilized (%)[a] |
|---|---|---|
| Fructose, C[b] | 107 | 10.4 ± 2.6[e] |
| Fructose, XXOC[c] | 112 | 76.1 ± 5.6[f] |
| Fructose, XXO[d] | 104 | 14.5 ± 3.7[e] |

[a]After 90 minutes of preincubation, spermatozoa were incubated with eggs for 2 hours. Eggs were then washed with fresh medium and incubated for another 22 hours before examination for fertilization. Values are means ± S.E.M. of 3 experiments.
[b]C represents catalase.
[c]XXOC represents the xanthine oxidase system: xanthine (X), xanthine oxidase (XO), and catalase (C).
[d]XXO represents the combination of xanthine and xanthine oxidase.
[e,f]Means with different superscripts differ (p < 0.05).

EXAMPLE 4

In the fourth series of experiments, 2 μM 6-aminonicotinamide (6-AN), an inhibitor of glucose-6-phosphate dehydrogenase, was added to the sperm suspension with and without XXOC in 5 different treatments before and after sperm capacitation: (1) the control treatment consisted of M-16 medium, (2) 6-AN was added to the control medium at 0 min, (3) 6-AN was added at 0 min and XXOC at 45 min, (4) 6-AN and XXOC were added at 0 min, and (5) 6-AN was added at 45 min. At 90 min, sperm were inseminated with eggs in vitro to assess fertilizing ability. In order to see the effect of these treatments on the percentages of capacitated and acrosome reacted sperm in a sperm population, sperm samples were taken from each treatment at 45 min and 90 min for CC assays. A parallel experimental design substituted 10 μM apocynin, an inhibitor of NADPH oxidase, for 6-AN.

Figure 2:
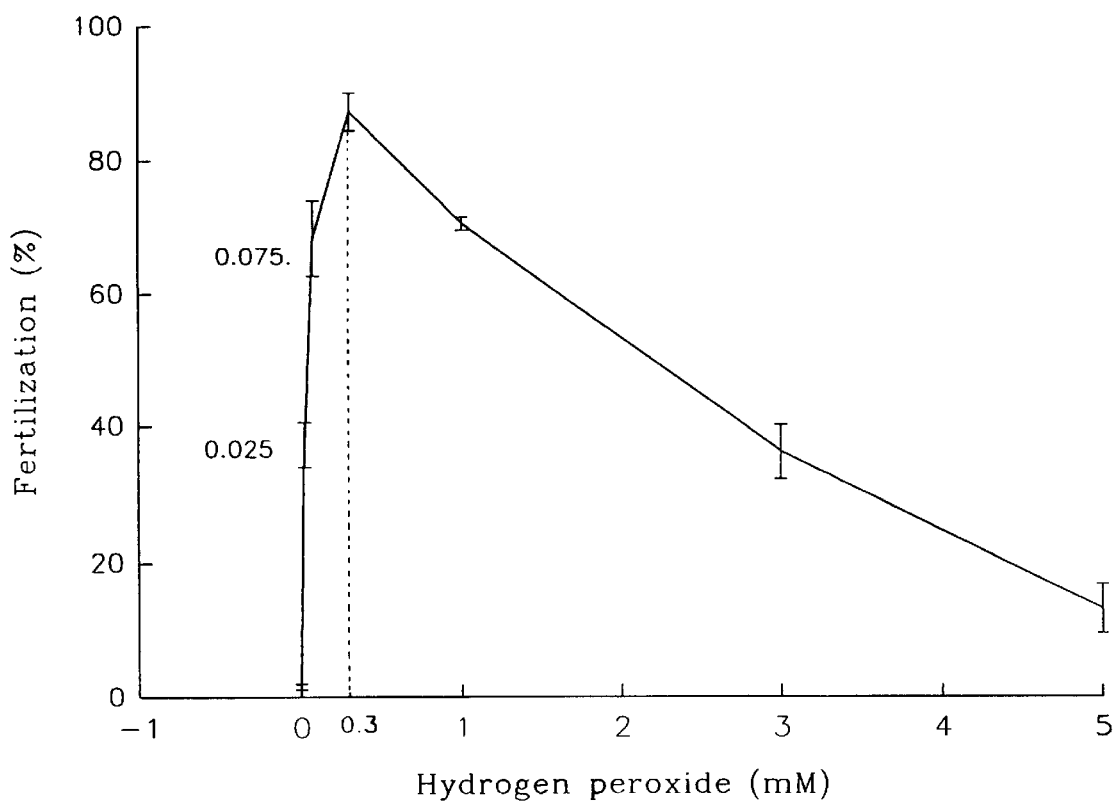
FIG. 2 is a graph showing fertilizing ability of mouse sperm in the presence of hydrogen peroxide without the presence of glucose. During 90 min of sperm incubation, spermatozoa were treated with $H_2O_2$ (0.025 mM–5 mM) at 0 min in the fructose medium. After 90 min of preincubation, spermatozoa were incubated with eggs in the fructose medium for 2 h. Eggs were then washed with fresh medium and incubated for another 22 h before examination for fertilization.
Figure 3A:
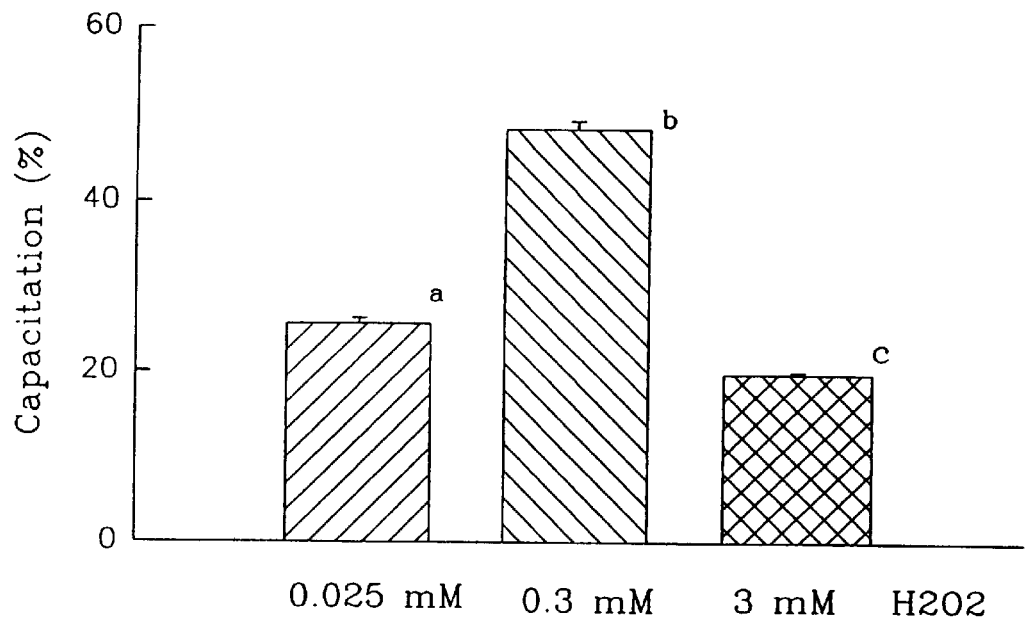
FIGS. 3A and 3B are graphs showing the effects of hydrogen peroxide on capacitation (FIG. 3A) and acrosome reaction (FIG. 3B) of mouse sperm in the fructose medium. Capacitated sperm displayed bright fluorescence over the anterior portion of the head and midpiece with a band which lacked fluorescence at the posterior portion of the head. At least 100 sperm per sample were examined at 45 min of sperm incubation. Acrosome reacted sperm displayed bright fluorescence on the midpiece and diminished fluorescence over the entire head. At least 100 sperm per sample were examined at 90 min of sperm incubation. (abc—Means with different superscripts differ ($p<0.05$).
Figure 3B:
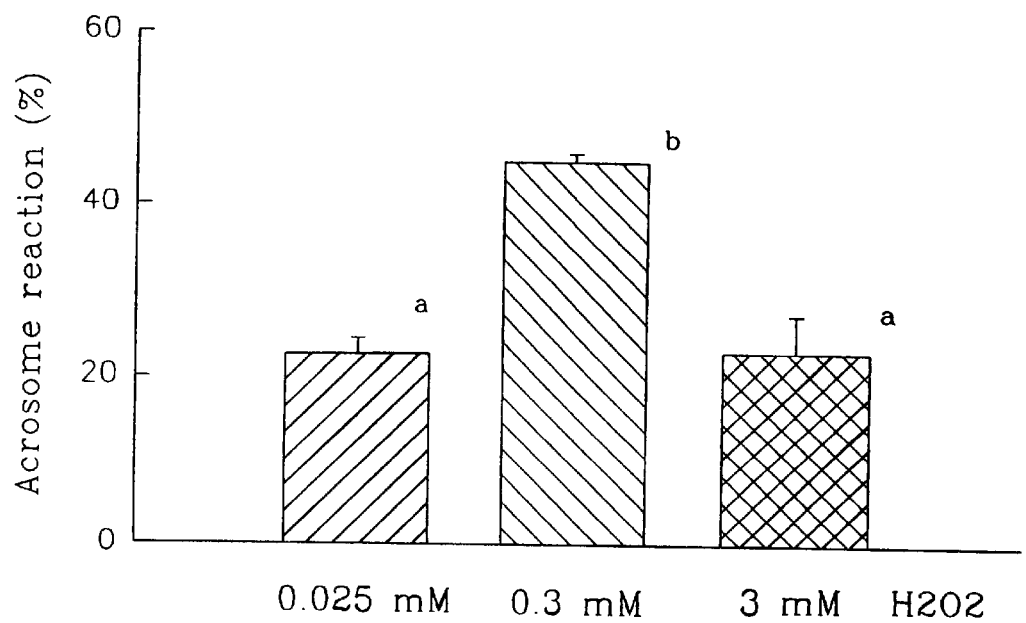
Figure 4A:
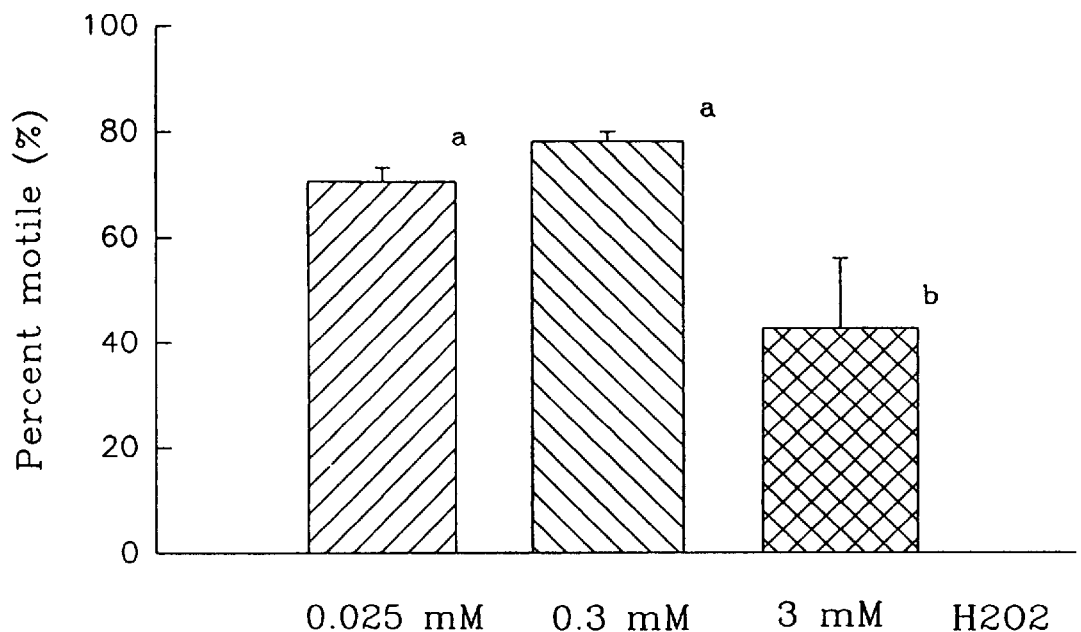
FIGS. 4A and 4B are graphs showing the effects of hydrogen peroxide on sperm motility (FIG. 4A) and curvilinear velocity (FIG. 4B). During 90 min of sperm incubation, spermatozoa were treated with $H_2O_2$ at 0 min in the fructose medium. For sperm motion assay, 20 ul aliquot of sperm suspension taken at 90 min of incubation was analyzed with a CELLSOFT computer-assisted digital image analysis system (CRYO Resources Inc., New York, 19698). A minimum of 100 sperm cells were analyzed to obtain measurements of percent motile sperm and curvilinear velocity. (ab—Means with different superscripts differ ($p<0.05$).
Figure 4B:
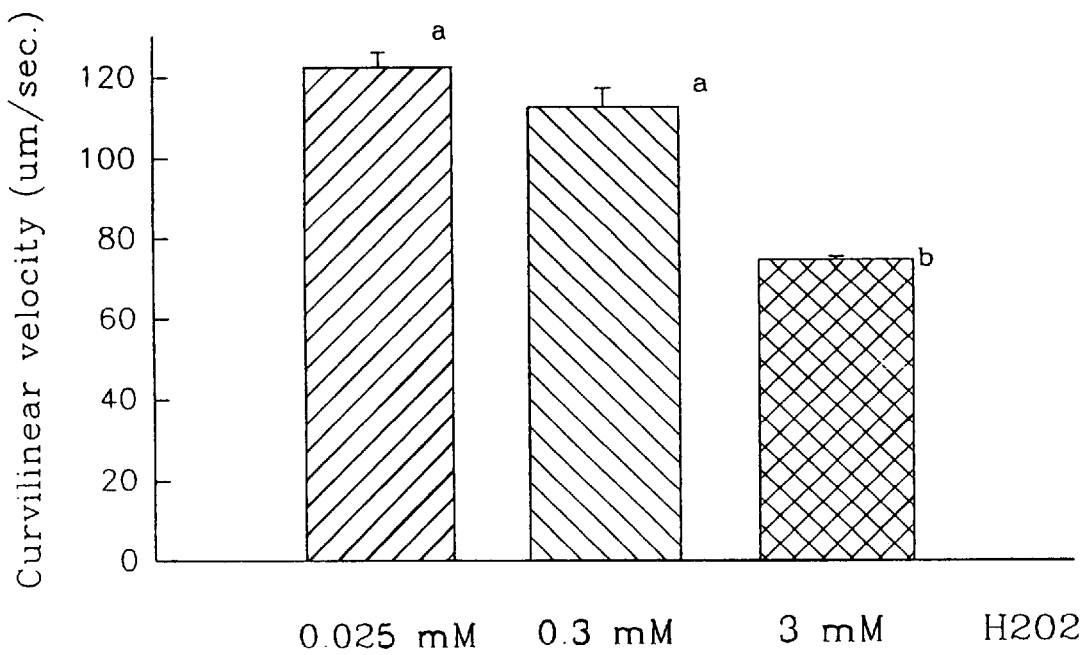

When different concentrations of $H_2O_2$ (0.025 mM, 0.075 mM, 0.3 mM, 1 mM, 3 mM, and 5 mM), instead of XXOC, were added to the media containing 5.56 mM fructose, 0.3 mM of $H_2O_2$ was the concentration that supported maximum fertilization (FIG. 2). The dose-response relationship clearly suggested that any concentration less than 0.3 mM was not sufficient to support sperm fertilizing ability, while any concentration greater than 0.3 mM was toxic (FIG. 2). This optimal concentration of $H_2O_2$ also supported maximum capacitation and acrosome reaction (FIG. 3). The percent of motile spermatozoa and curvilinear velocity (FIG. 4), however, were the same in 0.3 mM and lower concentrations. At higher concentrations, $H_2O_2$ decreased sperm motility and velocity.

The addition of 6-AN to the M-16 medium at 0 min of sperm incubation decreased sperm fertilizing ability to 34.8±2.6% (p<0.05 (Table 4).

TABLE 4

Inhibitory effect of 6-aminonicotinamide on fertilization.

| Treatments[a] | | No. of eggs observed | Fertilization[b] (%) |
|---|---|---|---|
| 0 min | 45 min | | |
| — | — | 100 | 95.0 ± 2.9[e] |
| 6-AN[c] | — | 77 | 34.8 ± 2.6[f] |
| 6-AN | XXOC[d] | 111 | 65.1 ± 3.2[g] |
| 6-AN, XXOC[d] | — | 103 | 91.8 ± 3.7[e] |

TABLE 4-continued

Inhibitory effect of 6-aminonicotinamide on fertilization.

| Treatments[a] | | No. of eggs observed | Fertilization[b] (%) |
|---|---|---|---|
| 0 min | 45 min | | |
| — | 6-AN | 84 | 81.5 ± 1.4[h] |

[a]During 90 minutes of sperm incubation, spermatozoa were treated with 6-AN or XXOC at either 0 or 45 minutes. Both the media of sperm incubation and fertilization were M-16 medium.
[b]After 90 minutes of preincubation, spermatozoa were incubated with eggs for 2 hours. Eggs were then washed with fresh medium and incubated for another 22 hours before examination for fertilization. Values are means ± S.E.M. of four experiments.
[c]6-AN is the abbreviation of 6-aminonicotinamide, which is an inhibitor of glucose-6-phosphate dehydrogenase.
[d]XXOC represents the xanthine oxidase system: xanthine (X), xanthine oxidase (XO), and catalase (C).
[efgh]Means with different superscripts differ (p < 0.05).

Figure 5A:
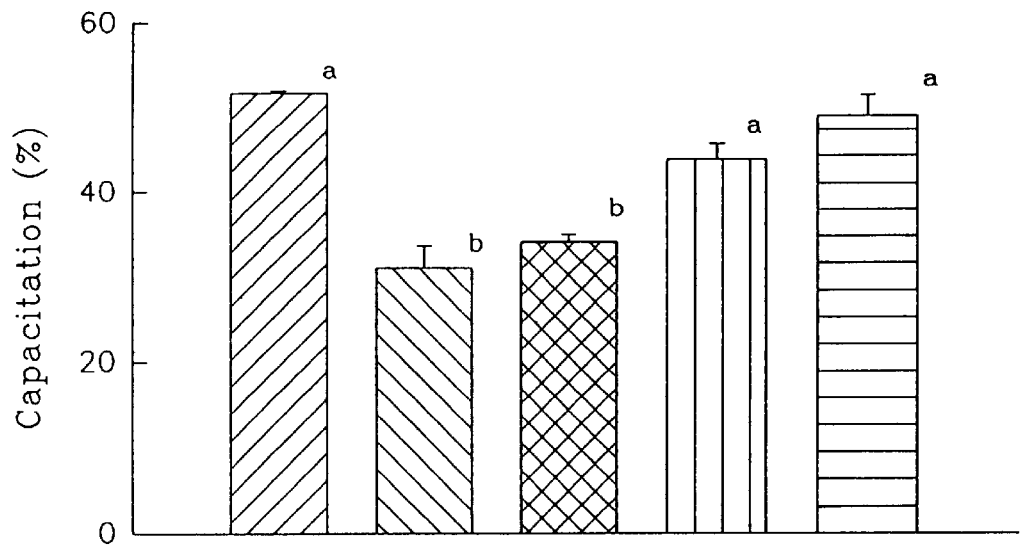
FIGS. 5A and 5B are graphs showing the inhibitory effect of 6-aminonicotinamide, an inhibitor of pentose phosphate pathway, on capacitation (FIG. 5A) and acrosome reaction (FIG. 5B). During 90 min of sperm incubation, spermatozoa were treated with 6-AN or XXOC at either 0 or 45 min in M-16 medium (containing glucose). Capacitated sperm displayed bright fluorescence over the anterior portion of the head and midpiece with a band which lacked fluorescence at the posterior portion of the head. At least 100 sperm per sample were examined at 45 min of sperm incubation. Acrosome reacted sperm displayed bright fluorescence on the midpiece and diminished fluorescence over the entire head. At least 100 sperm per sample were examined at 90 min of sperm incubation. (abc—Means with different superscripts differ ($p<0.05$).
Figure 5B:
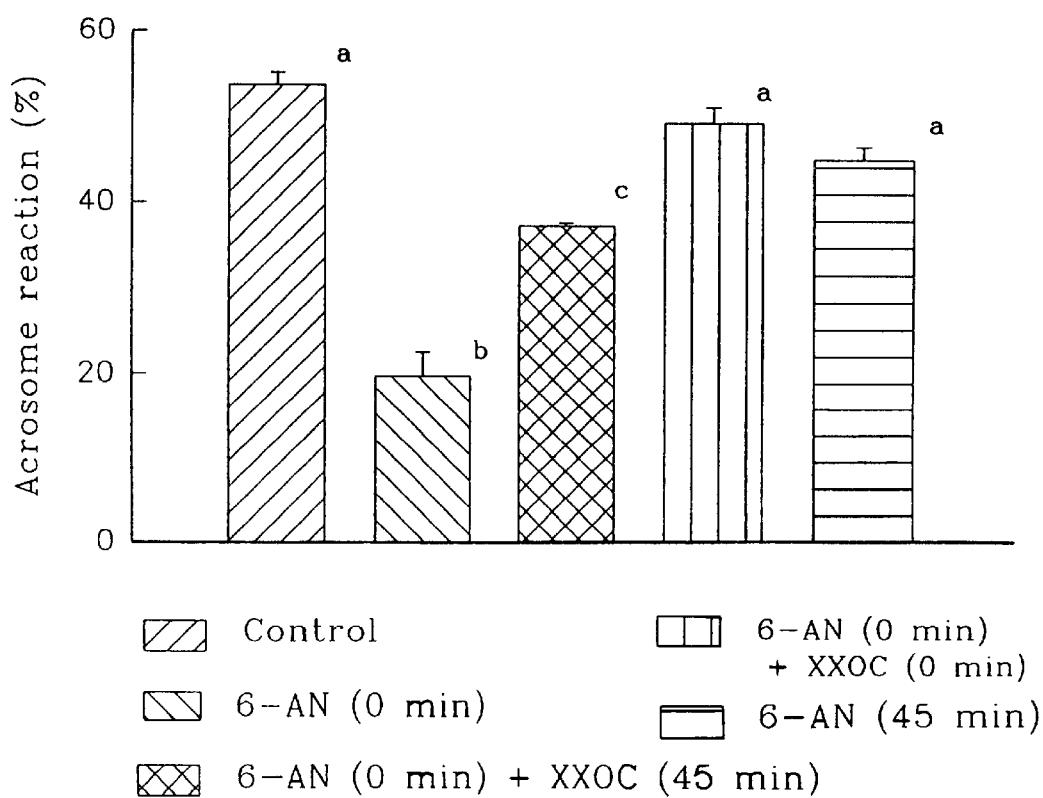

It also decreased the rate of sperm capacitation and acrosome reaction (FIG. 5). The additional presence of XXOC at 0 min and 45 min of sperm incubation reversed the inhibitory effect of 6-AN and resulted in 95.0±2.9% and 65.1±3.2% fertilization, respectively. The addition of XXOC also partially reversed the inhibitory effects of 6-AN on capacitation and acrosome reaction. This data demonstrated that reactive oxygen species generated from XXOC over-rode the 6-AN inhibition of glucose-6-phosphate dehydrogenase. The addition of 6-AN at 45 min, after significant amounts of spermatozoa had already capacitated, did not inhibit the acrosome reaction to the same extent as when it was added at 0 min.

In the parallel experiment, the addition of apocynin to the M-16 medium at 0 min of sperm incubation decreased sperm fertilizing ability to 33.9±3.1% (p<0.05) (Table 5).

TABLE 5

Inhibitory effect of apocynin on fertilization.

| Treatments[a] | | No. of eggs observed | Fertilization[b] (%) |
|---|---|---|---|
| 0 min | 45 min | | |
| — | — | 116 | 91.0 ± 2.4[e] |
| Apocynin[c] | — | 79 | 33.9 ± 3.1[f] |
| Apocynin | XXOC[d] | 106 | 71.9 ± 6.3[g] |
| Apocynin, XXOC[d] | — | 103 | 63.4 ± 5.2[g] |
| — | Apocynin | 109 | 82.6 ± 0.9[h] |

[a]During 90 minutes of sperm incubation, spermatozoa were treated with apocynin or XXOC at either 0 or 45 minutes. Both the media of sperm incubation and fertilization were M-16 medium.
[b]After 90 minutes of preincubation, spermatozoa were incubated with eggs for 2 hours. Eggs were then washed with fresh medium and incubated for another 22 hours before examination for fertilization. Values are means ± S.E.M. of four experiments.
[c]Apocynin is an inhibitor of NADPH oxidase.
[d]XXOC represents the xanthine oxidase system: xanthine (X), xanthine oxidase (XO), and catalase (C).
[efgh]Means with different superscripts differ (p < 0.05).

Figure 6A:
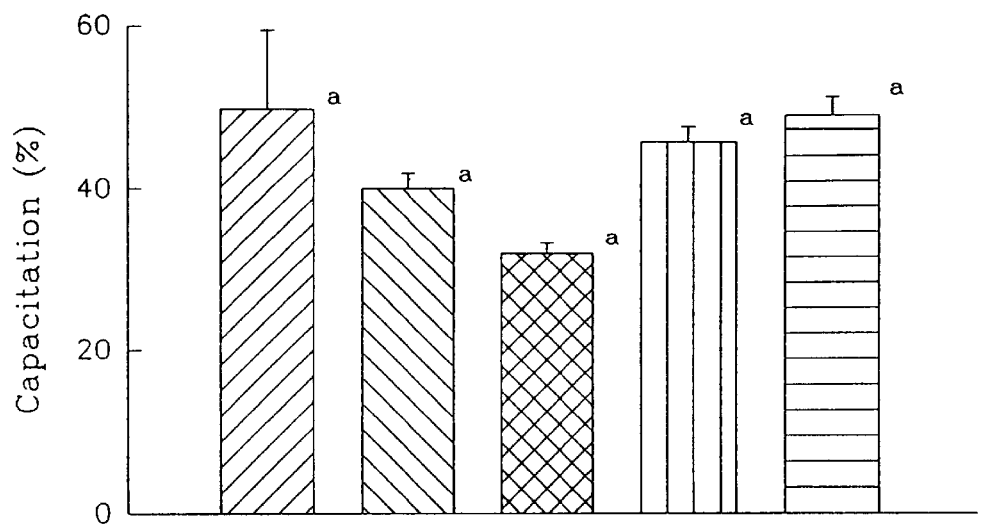
FIGS. 6A and 6B are graphs showing inhibitory effect of apocynin an inhibitor of NADPH oxidase, on capacitation (FIG. 6A) and acrosome reaction (FIG. 6B). During 90 min of sperm incubation, spermatozoa were treated with apocynin or XXOC at either 0 or 45 min in M-16 medium (containing glucose. Capacitated sperm displayed bright fluorescence over the anterior portion of the head and midpiece with a band which lacked fluorescence at the posterior portion of the head. At least 100 sperm per sample were examined at 45 min of sperm incubation. Acrosome reacted sperm displayed bright fluorescence on the midpiece and diminished fluorescence over the entire head. At least 100 sperm per sample were examined at 90 min of sperm incubation. (ab—Means with different superscripts differ ($p<0.05$).
Figure 6B:
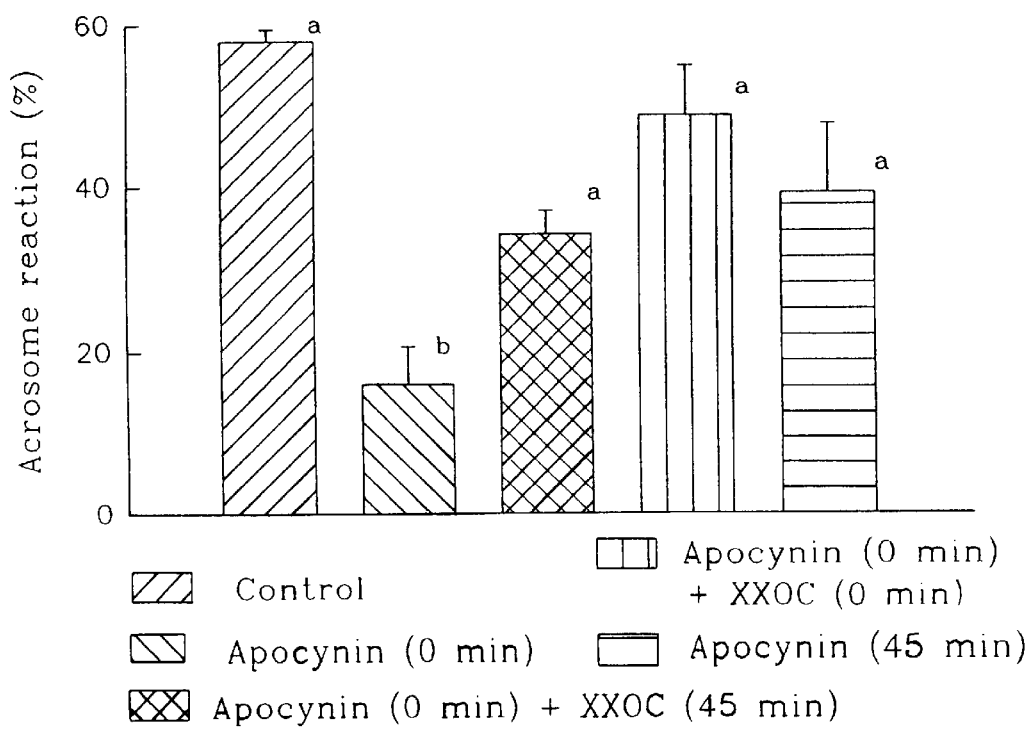

The additional presence of XXOC at 0 min and 45 min also revealed the trend of reversing he inhibitory effect on fertilization, capacitation, and the acrosome reaction as observed in the 6-AN/XXOC experiments (FIG. 6).

When encapsulated sperm are used in the present invention, the sperm can be released over time for capacitation by the reactive oxygen species. This increases the likelihood of fertilization at the proper time.

Statistics

Angular transformation was performed for the discrete quantitative parameters of percent motile spermatozoa, velocity, the percentage of eggs fertilized in vitro, and the percentage of capacitated and acrosome reacted spermatozoa. Those transformed data passing homogeneity of variance and normality tests were analyzed with the Student-Newman-Keuls multiple pairwise comparison by One Way Analysis of Variance (ANOVA) using SigmaStat 50 (1992).

It is intended that the foregoing description be only illustrative of the present invention and that the present invention be limited only by the hereinafter appended claims.

We claim:

1. A method for capacitating sperm for fertilization of an egg which comprises:
   (a) providing a sperm sample which is substantially free of glucose and reactive oxygen species and containing an exogenous glucose substitute carbohydrate source which is unable to capacitate the sperm in absence of the reactive oxygen species; and
   (b) adding an exogenous capacitating agent which comprises the reactive oxygen species to the sperm sample, whereby the sperm is capacitated for fertilization of the egg.

2. The method of claim 1 wherein glucose-6-phosphate dehydrogenase which is present in the sperm is inhibited in step (a).

3. The method of claim 1 wherein NADPH oxidase which is present in the sperm is inhibited in step (a).

4. The method of claim 1 wherein the glucose substitute carbohydrate source is selected from the group consisting of fructose and fructose-6-phosphate.

5. The method of claim 1 wherein the reactive oxygen species is provided by xanthine, xanthine oxidase and catalase which are added to the sample to produce the reactive oxygen species in the sample.

6. A method for fertilizing an egg with sperm which comprises:
   (a) providing a sperm sample which is substantially free of glucose and reactive oxygen species and containing an exogenous glucose substitute carbohydrate source which is unable to capacitate the sperm in absence of the reactive oxygen species;
   (b) adding exogenous capacitating agent which comprises the reactive oxygen species to the sperm sample whereby the sperm sample is capacitated for fertilization of the egg; and
   (c) fertilizing the egg with the capacitated sperm.

7. The method of claim 6 wherein the fertilization is in vitro.

8. The method of claim 6 wherein glucose-6-phosphate dehydrogenase which is present in the sperm is inhibited in step (a).

9. The method of claim 6 wherein NADPH oxidase which is present in the sperm is inhibited in step (a).

10. The method of claim 6 wherein the glucose substitute carbohydrate source is selected from the group consisting of fructose and fructose-6-phosphate.

11. The method of claim 6 wherein the reactive oxygen species is provided by xanthine, xanthine oxidase and catalase which are added to the sample to produce the reactive oxygen species in the sample.

12. A syringe apparatus for capacitating sperm for fertilization which comprises providing in a container (A) a sperm sample which is substantially free of glucose and reactive oxygen species and containing an exogenous glucose substitute carbohydrate source which is unable to capacitate the sperm in absence of the reactive oxygen species; and providing in a container (B) joined to container A to provide the syringe a capacitating agent which comprises the reactive oxygen species so that the sperm can be capacitated by mixing of the sperm sample and capacitating agent in containers (A) and (B) to provide a mixture (A) and (B) in a common chamber of the syringe from which is then expelled from the syringe.

13. The apparatus of claim 12 wherein the containers (A) and (B) are joined together and each is constructed as a syringe with a plunger in a barrel and wherein each barrel leads to a common outlet opposite the plunger, so that (A) and (B) are mixed together upon pushing the plungers into the barrel to thereby capacitate the sperm.

14. The apparatus of any one of claims 12 or 13 wherein glucose-6-phosphate dehydrogenase which is present in the sperm sample is inhibited in container (A).

15. The apparatus of any one of claims 12 or 13 wherein NADPH oxidase which is present in the sperm sample is inhibited in step (a).

16. The apparatus of any one of claims 12 or 13 wherein the glucose substitute carbohydrate source is selected from the group consisting of fructose and fructose-6-phosphate dehydrogenase.

17. The apparatus of any one of claims 12 or 13 wherein the reactive oxygen species is provided by xanthine, xanthine oxidase and catalase which are added to the sample to produce the reactive oxygen species in the sample.

18. The apparatus of any one of claims 12 or 13 wherein the containers (A) and (B) are preserved in a frozen form and thawed for use.

19. A test kit for detecting an ability of sperm in a sample to be capacitated wherein the sperm is substantially free of glucose, and reactive oxygen species which comprises:

(a) a glucose substitute carbohydrate source which is unable to capacitate the sperm in absence of the reactive oxygen species;

(b) a container (A) containing an exogenous capacitating agent which comprises a reactive oxygen species which can capacitate the sperm; and (c) a container (B) containing a fluorescent reagent which reacts with the sperm to produce a detectable indication of capacitation of the sperm and thus the ability to be capacitated.

20. The test kit of claim 19 wherein the reagent is a fluorescent molecule labeled chlortetracycline.

21. The method of claim 1 wherein the reactive oxygen species is provided by hydrogen peroxide.

22. The syringe of claim 12 wherein the reactive oxygen species is provided by hydrogen peroxide in container (B).

23. The kit of claim 19 wherein the reactive oxygen species is provided by hydrogen peroxide in container (A).

* * * * *